United States Patent
Shum

(10) Patent No.: US 11,447,819 B2
(45) Date of Patent: Sep. 20, 2022

(54) METHODS FOR 3' OVERHANG REPAIR

(71) Applicant: GUARDANT HEALTH, INC., Redwood City, CA (US)

(72) Inventor: Eleen Shum, San Carlos, CA (US)

(73) Assignee: GUARDANT HEALTH, INC., Palo Alto, CA (US)

( * ) Notice: Subject to any disclaimer, the term of this patent is extended or adjusted under 35 U.S.C. 154(b) by 161 days.

(21) Appl. No.: 17/079,268

(22) Filed: Oct. 23, 2020

(65) Prior Publication Data

US 2021/0123097 A1    Apr. 29, 2021

Related U.S. Application Data

(60) Provisional application No. 62/926,093, filed on Oct. 25, 2019.

(51) Int. Cl.
*C12Q 1/6855* (2018.01)
*C12Q 1/6806* (2018.01)

(52) U.S. Cl.
CPC ......... *C12Q 1/6855* (2013.01); *C12Q 1/6806* (2013.01)

(58) Field of Classification Search
CPC ......................... C12Q 2533/101; C12Q 1/6855
See application file for complete search history.

(56) References Cited

U.S. PATENT DOCUMENTS

| | | | |
|---|---|---|---|
| 6,582,908 | B2 | 6/2003 | Fodor et al. |
| 7,537,898 | B2 | 5/2009 | Bost et al. |
| 9,598,731 | B2 | 3/2017 | Talasaz |
| 9,850,523 | B1 | 12/2017 | Chudova et al. |
| 9,902,992 | B2 | 2/2018 | Talasaz et al. |
| 2001/0053519 | A1 | 12/2001 | Fodor et al. |
| 2003/0152490 | A1 | 8/2003 | Trulson et al. |
| 2004/0209299 | A1* | 10/2004 | Pinter ............... C12N 15/1093 536/25.4 |
| 2011/0160078 | A1 | 6/2011 | Fodor et al. |
| 2012/0172258 | A1 | 7/2012 | Eshoo et al. |

FOREIGN PATENT DOCUMENTS

| | | |
|---|---|---|
| EP | 1647602 A1 | 4/2006 |
| WO | 2016093838 A1 | 6/2016 |
| WO | 2020099675 A1 | 5/2020 |

OTHER PUBLICATIONS

International search report and written opinion dated Feb. 2, 2020 for PCT/US2020/057189.

Rohland, N. et al. "Cost-effective, high-throughput DNA sequencing libraries for multiplexed target capture" Genome Res (2012) 22(5):939-946.

Yegnasubramanian, S. "Preparation of fragment libraries for next-generation sequencing on the applied biosystems SOLiD platform" Methods in Enzymology (2013) 529:185-200.

* cited by examiner

*Primary Examiner* — Teresa E Strzelecka
(74) *Attorney, Agent, or Firm* — Timothy A. Hott

(57) ABSTRACT

Methods of repairing a partially double-stranded DNA fragment are provided. In some embodiments, the methods comprise (a) contacting the partially double-stranded DNA fragment with one or more primers of a primer population, wherein the partially double-stranded DNA fragment comprises a 3' overhang and the primer population comprises a random target-hybridizing sequence; (b) extending one or more primers of the primer population along the DNA fragment using a DNA polymerase, thereby producing one or more extended primers annealed to the DNA fragment; and (c) ligating the 3' end of one or more extended primers to the 5' end of an extended primer or a strand of the partially double-stranded DNA fragment, thereby providing a repaired DNA fragment.

20 Claims, 3 Drawing Sheets

Specification includes a Sequence Listing.

SEQUENCE LISTING

```
<160> NUMBER OF SEQ ID NOS: 3

<210> SEQ ID NO 1
<211> LENGTH: 58
<212> TYPE: DNA
<213> ORGANISM: Artificial Sequence
<220> FEATURE:
<223> OTHER INFORMATION: TruSq Universal Adapter

<400> SEQUENCE: 1
aatgatacgg cgaccaccga gatctacact ctttccctac acgacgctct tccgatct          58

<210> SEQ ID NO 2
<211> LENGTH: 63
<212> TYPE: DNA
<213> ORGANISM: Artificial Sequence
<220> FEATURE:
<223> OTHER INFORMATION: TruSeq Index Adapter
<220> FEATURE:
<221> NAME/KEY: misc_feature
<222> LOCATION: (34)..(39)
<223> OTHER INFORMATION: n is a, c, g, t, or u

<400> SEQUENCE: 2
gatcggaaga gcacacgtct gaactccagt cacnnnnnna tctcgtatgc cgtcttctgc        60
ttg                                                                      63

<210> SEQ ID NO 3
<211> LENGTH: 58
<212> TYPE: DNA
<213> ORGANISM: Artificial Sequence
<220> FEATURE:
<223> OTHER INFORMATION: Exemplary Y-shaped adapter

<400> SEQUENCE: 3
aatgatacgg cgaccaccga gatctacact ctttccctac acgacgctct tccgatcc          58
```

METHODS FOR 3' OVERHANG REPAIR

CROSS-REFERENCE TO RELATED APPLICATIONS

This application claims the benefit of priority of U.S. Provisional Patent Application No. 62/926,093, filed Oct. 25, 2019, which is incorporated herein by reference in its entirety for all purposes.

SEQUENCE LISTING

The instant application contains a Sequence Listing which has been filed electronically in ASCII format and is hereby incorporated by reference in its entirety. Said ASCII copy, created on Oct. 21, 2020, is named 2020-10-23_GH0054US_Sequence_Listing_ST25.txt and is 970 bytes in size.

INTRODUCTION AND SUMMARY

Repair of overhangs that occur in certain types of DNA molecules is an important step in preparing the molecules for further analysis, such as sequencing and/or amplification. For example, 3' overhangs, in which a number of nucleotides near the 3' end of a molecule are single-stranded, can occur in sheared DNA and cell-free DNA, e.g., obtained from blood samples. It can be desirable to convert 3' overhangs to blunt ends or to a single-base overhang for compatibility with subsequent steps such as ligation of a tag, barcode, or adapter.

Existing methods for overhang repair use a 3' to 5' exonuclease to resect the 3' overhang. This approach results in loss of information in that nucleotides are removed and the location of the end of the original molecule cannot be determined. Thus, 3' overhang repair by exonucleolysis can prevent one from obtaining information regarding, e.g., the sequence of the bases between the 5' and 3' ends as well as nucleosome positioning. Accordingly, there is a need for improved methods of 3' overhang repair. The present disclosure aims to meet this need, provide other benefits, or at least provide the public with a useful choice.

Accordingly, the following embodiments are provided. Embodiment 1 is a method of repairing a partially double-stranded DNA fragment, the method comprising:
(a) contacting the partially double-stranded DNA fragment with one or more primers of a primer population, wherein the partially double-stranded DNA fragment comprises a 3' overhang and the primer population comprises a random target-hybridizing sequence;
(b) extending one or more primers of the primer population along the DNA fragment using a DNA polymerase, thereby producing one or more extended primers annealed to the DNA fragment; and
(c) ligating the 3' end of one or more extended primers to the 5' end of an extended primer or a strand of the partially double-stranded DNA fragment, thereby providing a repaired DNA fragment.

Embodiment 2 is the method of any one of the preceding embodiments, wherein the DNA polymerase lacks 3' to 5' exonuclease activity.

Embodiment 3 is the method of any one of the preceding embodiments, wherein the DNA polymerase lacks 5' to 3' exonuclease activity.

Embodiment 4 is the method of any one of the preceding embodiments, wherein the DNA polymerase lacks strand displacement activity.

Embodiment 5 is the method of any one of the preceding embodiments, wherein the DNA polymerase is a Klenow fragment.

Embodiment 6 is the method of the immediately preceding embodiment, wherein the DNA polymerase is an exo- Klenow fragment.

Embodiment 7 is the method of any one of the preceding embodiments, wherein the partially double-stranded DNA fragment has 3' overhangs at each end.

Embodiment 8 is the method of any one of the preceding embodiments, wherein the partially double-stranded DNA fragment has a 3' overhang and (i) a blunt end or (ii) a 5' overhang.

Embodiment 9 is the method of the immediately preceding embodiment, wherein the 5' overhang is repaired by extending the 3' end along the 5' overhang.

Embodiment 10 is the method of any one of the preceding embodiments, wherein the partially double-stranded DNA fragment is from a bodily fluid sample.

Embodiment 11 is the method of the immediately preceding embodiment, wherein the bodily fluid is whole blood, serum, plasma, or urine.

Embodiment 12 is the method of any one of the preceding embodiments, wherein the partially double-stranded DNA fragment is a cfDNA fragment.

Embodiment 13 is the method of any one of the preceding embodiments, wherein the partially double-stranded DNA fragment is mammalian.

Embodiment 14 is the method of any one of the preceding embodiments, wherein the partially double-stranded DNA fragment is human.

Embodiment 15 is the method of any one of the preceding embodiments, wherein the partially double-stranded DNA fragment is part of a population of DNA fragments in a composition.

Embodiment 16 is the method of the immediately preceding embodiment, wherein the population of DNA fragments comprise sheared DNA.

Embodiment 17 is the method of embodiment 15 or 16, wherein the population of DNA fragments comprise epigenetically modified DNA.

Embodiment 18 is the method of any one of embodiments 15-17, wherein the population of DNA fragments comprises fragments from a plurality of genomic loci.

Embodiment 19 is the method of any one of embodiments 15-18, wherein the population of DNA fragments is non-enriched.

Embodiment 20 is the method of any one of embodiments 15-19, wherein the population of DNA fragments is unamplified.

Embodiment 21 is the method of any one of the preceding embodiments, wherein the random target-hybridizing sequence has a length of at least 4, 5, 6, 7, 8, 9, or 10 nucleotides.

Embodiment 22 is the method of any one of the preceding embodiments, wherein the random target-hybridizing sequence has a length of about 4, 5, 6, 7, 8, 9, 10, 11, or 12 nucleotides.

Embodiment 23 is the method of any one of the preceding embodiments, wherein the primers of the primer population are single-stranded.

Embodiment 24 is the method of any one of embodiments 1-20, wherein the primers of the primer population are double-stranded with a 3' overhang and the random target-hybridizing sequence is in the 3' overhang.

Embodiment 25 is the method of any one of embodiments 1-20, wherein the primers of the primer population are hairpins with a 3' overhang and the random target-hybridizing sequence is in the 3' overhang.

Embodiment 26 is the method of any one of embodiments 21-22, wherein the hairpin or double-stranded region of the primers comprises an adapter.

Embodiment 27 is the method of any one of embodiments 21-23, wherein the hairpin or double-stranded region of the primers comprises a tag.

Embodiment 28 is the method of embodiment 24, wherein the tag comprises a barcode.

Embodiment 29 is the method of embodiment 25, wherein the primer population comprises a plurality of different barcodes.

Embodiment 30 is the method of any one of the preceding embodiments, wherein at least steps (a)-(c) are performed in a single tube.

Embodiment 31 is the method of any one of the preceding embodiments, wherein the double-stranded DNA fragment is in a composition and for at least steps (a)-(c) no component is removed from the composition.

Embodiment 32 is the method of any one of the preceding embodiments, wherein the repaired DNA fragment comprises one or two blunt ends, or the method further comprises blunting one or two ends of the repaired DNA fragment.

Embodiment 33 is the method of the immediately preceding embodiment, further comprising end-tailing the repaired DNA fragment using a polymerase that performs a non-template directed addition of a nucleotide to the 3' ends of blunt-ended nucleic acids, optionally wherein A is added preferentially to G preferentially to C or T.

Embodiment 34 is the method of any one of the preceding embodiments, further comprising ligating a tag to the repaired DNA fragment (optionally at both ends), optionally wherein the tag comprises a barcode and/or adapter.

Embodiment 35 is the method of any one of the preceding embodiments, further comprising purifying the repaired DNA fragment.

Embodiment 36 is the method of any one of the preceding embodiments, further comprising denaturing one or more enzymes used in step (b) and/or (c) after step (b) and/or (c).

Embodiment 37 is the method of any one of the preceding embodiments, further comprising amplifying the repaired DNA fragment.

Embodiment 38 is the method of the immediately preceding embodiment, wherein the repaired DNA fragment comprises one or more adapters (e.g., two adapters) and amplifying the repaired DNA fragment uses one or more (e.g., two) amplification oligomers that anneal to the one or more adapters.

Embodiment 39 is the method of any one of the preceding embodiments, further comprising enriching the repaired DNA fragments for fragments of interest, thereby providing enriched DNA fragments, optionally wherein the enriching step is performed after an amplification step.

Embodiment 40 is the method of the immediately preceding embodiment, wherein the fragments of interest comprise loci that vary in a disease or disorder-associated manner, optionally wherein the disease or disorder is a cancer.

Embodiment 41 is the method of the immediately preceding embodiment, wherein the variation is one or more of single nucleotide variation, copy number variation, gene fusion, or indels.

Embodiment 42 is the method of the immediately preceding embodiment, wherein the fragments of interest comprise one, two, three, or four of fragments that show single nucleotide disease or disorder-associated variation; copy number disease or disorder-associated variation; disease or disorder-associated gene fusion; or disease or disorder-associated indels, optionally wherein the disease or disorder is cancer.

Embodiment 43 is the method of any one of embodiments 36-39, further comprising amplifying the enriched DNA fragments.

Embodiment 44 is the method of any one of the preceding embodiments, further comprising sequencing the repaired DNA fragment.

Embodiment 45 is the method of the immediately preceding embodiment wherein the sequencing sequences a nucleotide that formed a 3' overhang in the partially double-stranded DNA fragment.

Embodiment 46 is the method of embodiment 41 or 42, wherein the sequencing is high-throughput sequencing.

Embodiment 47 is the method of any one of embodiments 44-46, wherein a plurality of repaired DNA fragments are generated and at least a portion of the repaired DNA fragments comprise tags, and the sequencing generates a plurality of sequence reads from a plurality of repaired DNA fragments.

Embodiment 48 is the method of embodiment 47, wherein the sequence reads comprise sequence of nucleotides that formed a 3' overhang in the partially double-stranded DNA fragment and sequence of a tag.

In some embodiments of each and every aspect of the invention, the results of the systems and/or methods disclosed herein are used as an input to generate a report. The report may be in a paper or electronic format. For example, information on the presence or absence of cancer, as determined by the methods or systems disclosed herein, can be displayed in such a report. Alternatively or additionally, the report may comprise information relating to or derived from the identity of nucleobases in the sample. The methods or systems disclosed herein may further comprise a step of communicating the report to a third party, such as the subject from whom the sample is derived or a health care practitioner.

The various steps of the methods disclosed herein, or the steps carried out by the systems disclosed herein, may be carried out at the same time or different times, and/or in the same geographical location or different geographical locations, e.g. countries. The various steps of the methods disclosed herein can be performed by the same person or different people.

DETAILED DESCRIPTION OF CERTAIN EMBODIMENTS

Figure 1:
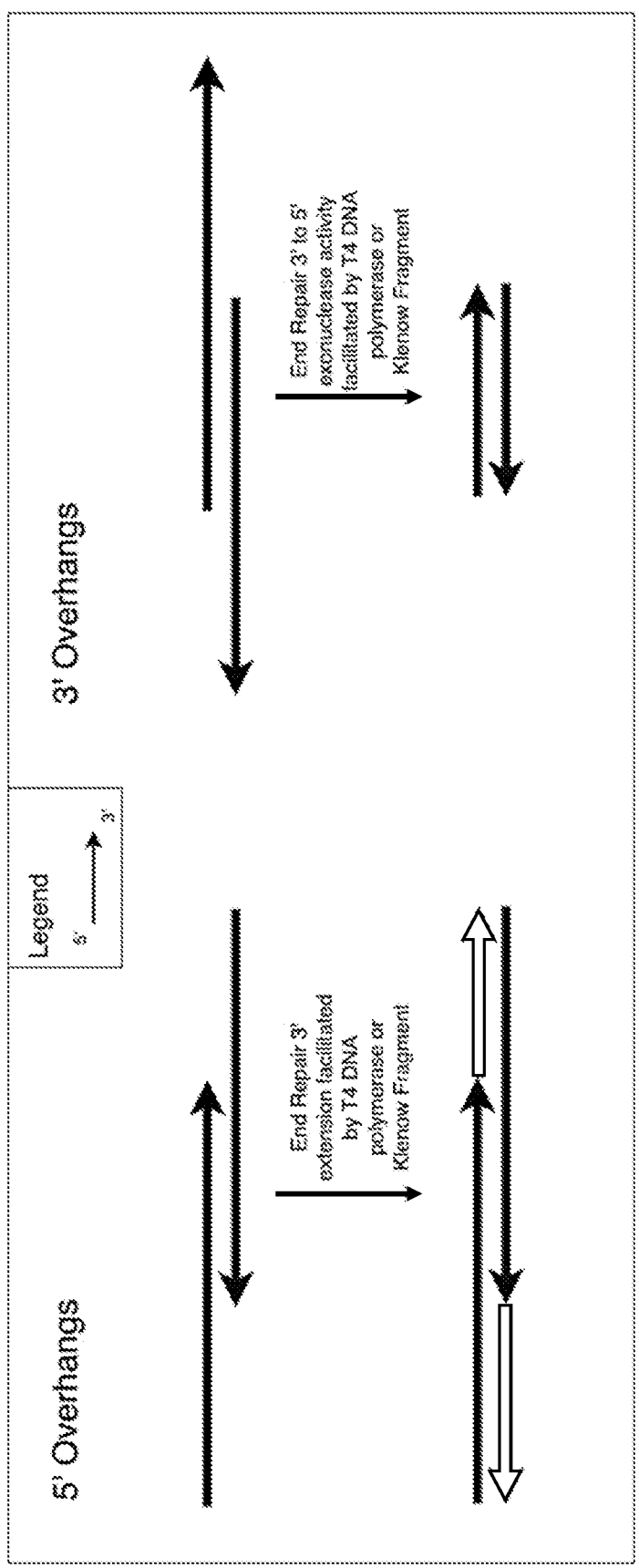
FIG. 1 illustrates 5' overhangs, 3' overhangs, and existing methods for end repair.
Figure 2:
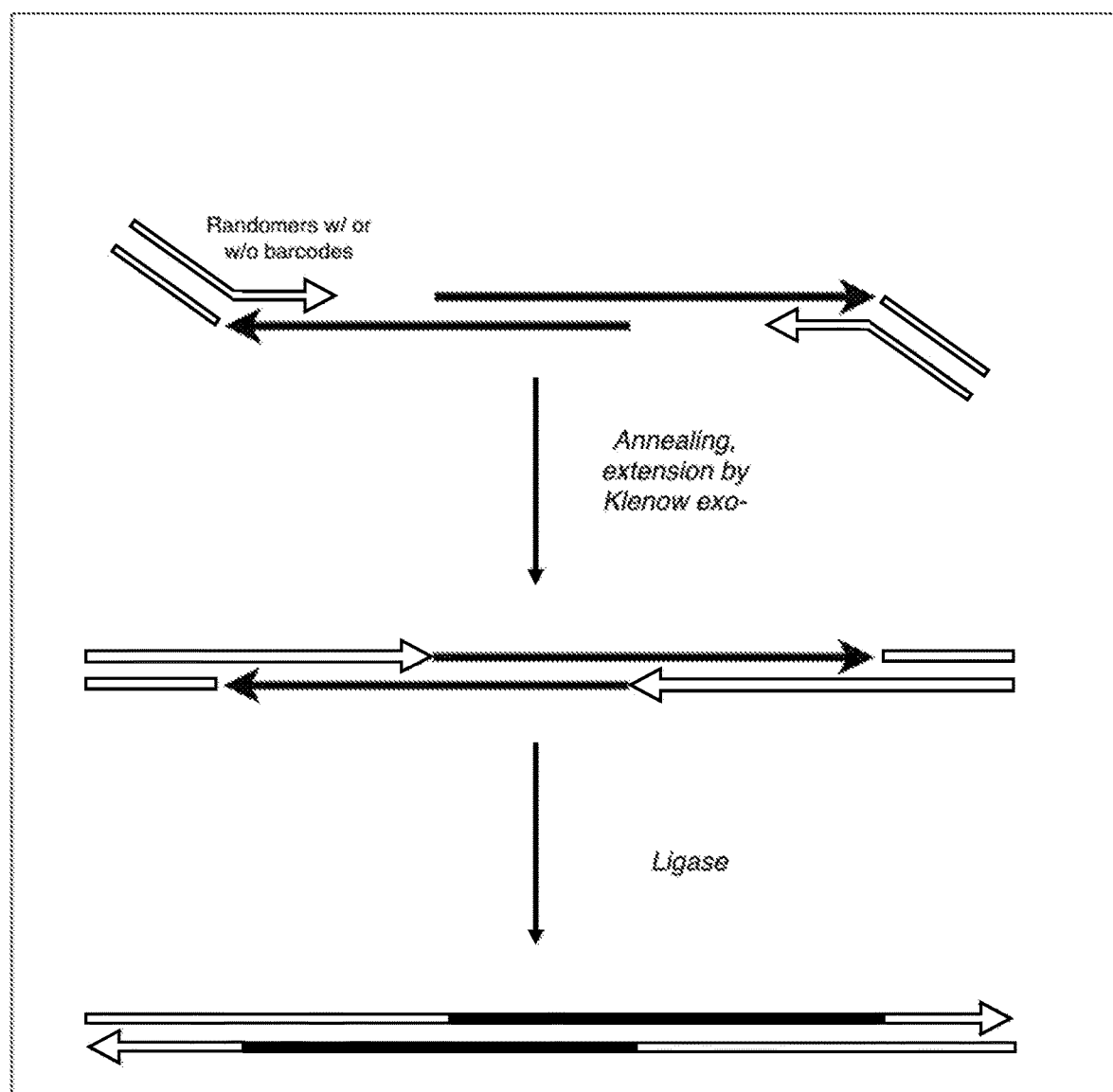
FIG. 2 illustrates an embodiment of 3' overhang repair according to this disclosure in which primers comprising a 3' random sequence and a 5' double stranded sequence (e.g., comprising a barcode, adapter, or tag) are annealed to a partially double-stranded DNA fragment. Extension, e.g., with Klenow exo-, and ligation provides a repaired molecule which retains the sequence of the 3' overhangs.
Figure 3:
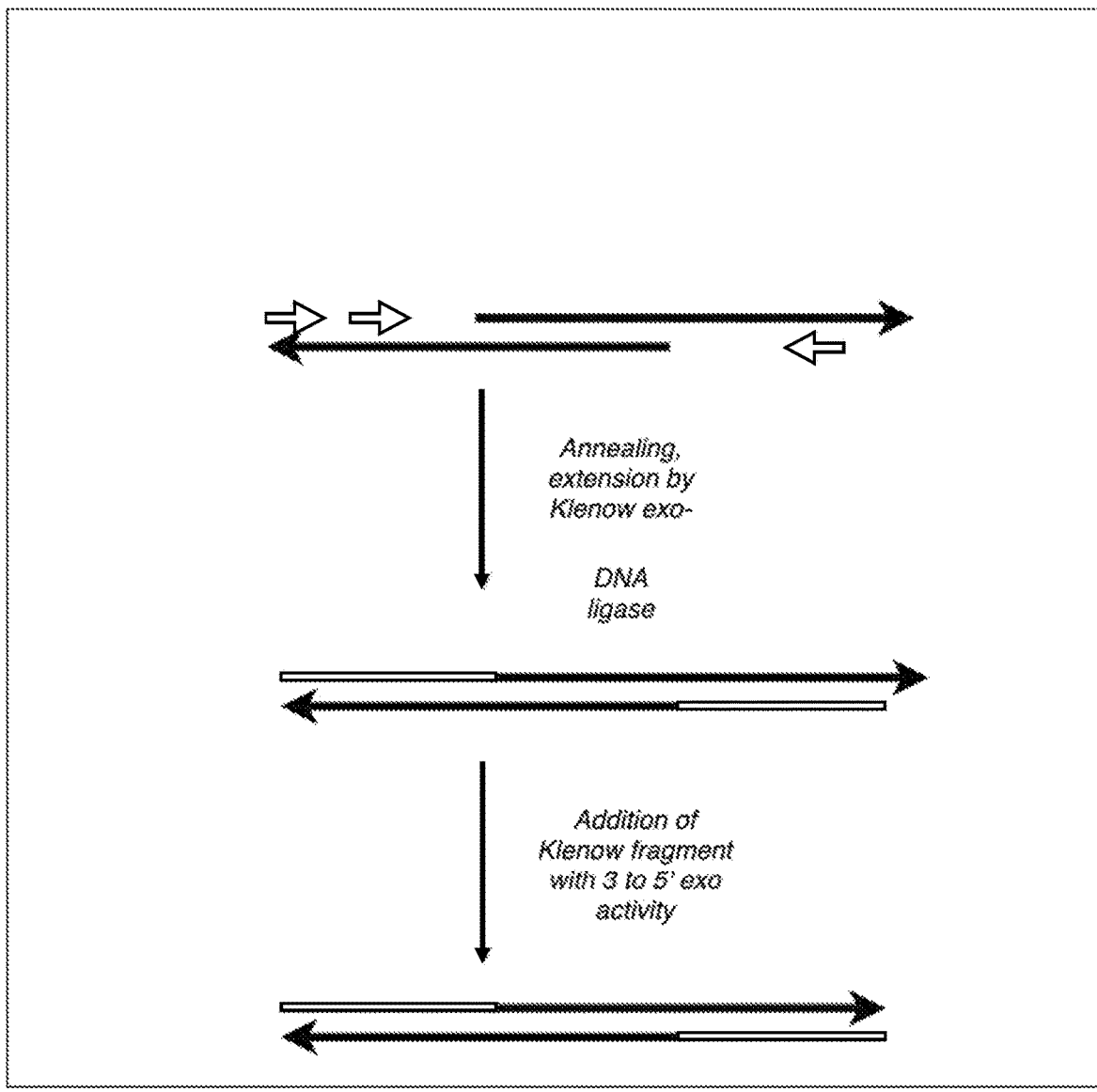
FIG. 3 illustrates an embodiment of 3' overhang repair according to this disclosure in which primers having a random sequence are annealed to a partially double-stranded DNA fragment. Extension, e.g., with Klenow exo-, and ligation provides a repaired molecule which retains the sequence of the 3' overhangs.

The section headings used herein are for organizational purposes only and are not to be construed as limiting the subject matter described.

All references cited herein, including patent applications, patent publications, and Genbank Accession numbers are herein incorporated by reference, as if each individual reference were specifically and individually indicated to be incorporated by reference in its entirety.

Definitions

Unless otherwise defined, scientific and technical terms used in connection with the present disclosure shall have the meanings that are commonly understood by those of ordinary skill in the art. Further, unless otherwise required by context or expressly indicated, singular terms shall include pluralities and plural terms shall include the singular. For any conflict in definitions between various sources or references, the definition provided herein will control.

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "an oligomer" includes a plurality of oligomers and the like. In this application, the use of "or" means "and/or" unless expressly stated or understood by one skilled in the art. In the context of a multiple dependent claim, the use of "or" refers back to more than one preceding independent or dependent claim.

It will be appreciated that there is an implied "about" prior to the temperatures, concentrations, times, etc. discussed in the present disclosure, such that slight and insubstantial deviations are within the scope of the present teachings herein. In general, the term "about" indicates insubstantial variation in a quantity of a component of a composition not having any significant effect on the activity or stability of the composition. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings. To the extent that any material incorporated by reference is inconsistent with the express content of this disclosure, the express content controls.

Unless specifically noted, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

A subject refers to an animal, such as a mammalian species (preferably human) or avian (e.g., bird) species, or other organism, such as a plant. More specifically, a subject can be a vertebrate, e.g., a mammal such as a mouse, a primate, a simian or a human. Animals include farm animals, sport animals, and pets. A subject can be a healthy individual, an individual that has or is suspected of having a disease or a predisposition to the disease, or an individual that is in need of therapy or suspected of needing therapy.

A genetic variant refers to an alteration, variant or polymorphism in a nucleic acid sample or genome of a subject. Such alteration, variant or polymorphism can be with respect to a reference genome, which may be a reference genome of the subject or other individual. Variations include one or more single nucleotide variations (SNVs), insertions, deletions, repeats, small insertions, small deletions, small repeats, structural variant junctions, variable length tandem repeats, and/or flanking sequences, copy number variants (CNVs), transversions and other rearrangements are also forms of genetic variation. A variation can be a base change, insertion, deletion, repeat, copy number variation, transversion, or a combination thereof.

A cancer marker is a genetic variant associated with presence or risk of developing a cancer. A cancer marker can provide an indication a subject has cancer or a higher risk of developing cancer than an age and gender matched subject of the same species. A cancer marker may or may not be causative of cancer.

A nucleic acid tag is a short nucleic acid (e.g., less than 100, 50 or 10 nucleotides long), usually of artificial sequence and usually DNA, used to label repaired DNA fragments to distinguish nucleic acids that are (i) from different samples (e.g., representing a sample index), (ii) of different types, or (iii) which have undergone different processing. Tags can be single- or double-stranded. Nucleic tags can be decoded to reveal information such as the sample of origin, form or processing of a nucleic acid. Tags can be used to allow pooling and parallel processing of multiple nucleic acids bearing different tags with the nucleic acids subsequently being deconvoluted by reading the tags. Tags can also be referred to as molecular identifiers or barcodes.

Adapters are short nucleic acids (e.g., less than 500, 100 or 50 nucleotides long and typically DNA) for linkage to either or both ends of a repaired DNA fragment molecule. An adapter may be, but is not necessarily, provided in double-stranded form for ligation. An adapter can also be provided, e.g., as a 5' element in a primer (such as a member of a population of primers with randomized target-hybridizing sequence) where it may be, e.g., single-stranded, a hairpin or double-stranded. Adapters can include primer binding sites to permit amplification of a repaired DNA fragment molecule flanked by adapters at both ends, and/or a sequencing primer binding site, including primer binding sites for a next generation sequencing procedure. Adapters can also include binding sites for capture probes, such as an oligonucleotide attached to a flow cell support. Adapters can also include a tag as described herein. Tags may be positioned relative to primer and sequencing primer binding sites such that the tag is included in amplicons and sequencing reads of a repaired DNA fragment. The same or different adapters can be linked to the respective ends of a sample molecule. Sometimes the same adapter is linked to the respective ends except that the tag is different. An exemplary type of adapter is a Y-shaped adapter in which one end is blunt ended or tailed as described herein, for joining to a nucleic acid (e.g., repaired DNA fragment), which is also blunt ended or tailed with a complementary nucleotide. Another exemplary type of adapter is a bell-shaped adapter, likewise with a blunt or tailed end for joining to a nucleic acid to be analyzed.

A "partially double stranded DNA fragment" refers to a linear DNA that is partially double-stranded and partially single-stranded.

A "3' overhang" refers to one or more consecutive nucleotides at the 3' end of a partially double stranded DNA fragment that are not annealed to complementary nucleotides.

The interchangeable terms "oligomer," "oligo," and "oligonucleotide" refer to a nucleic acid having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 12 to 15 nt and an upper limit of about 50 to 600 nt, and other embodiments are in a range having a lower limit of about 15 to 20 nt and an upper limit of about 22 to 100 nt. Oligonucleotides may be purified from naturally occurring sources or may be synthesized using any of a variety of well-known enzymatic or chemical methods. The term oligonucleotide does not denote any particular function to the reagent; rather, it is used generically to cover all such reagents described herein. An oligonucleotide may serve various different functions. For example, it may function as a primer if it is capable of hybridizing to a complementary strand and can further be extended in the presence of a nucleic acid polymerase; and it may function to detect a target nucleic acid if it is capable of hybridizing to the target nucleic acid, or an amplicon thereof, and further provides a detectible moiety (e.g., a fluorophore).

A "primer" is an oligonucleotide comprising a 3' end capable of being extended by a polymerase.

A primer population that "comprises a random target-hybridizing sequence" is a plurality of primers in which the target-hybridizing sequence is variable rather than constant. For example, a random target-hybridizing sequence may comprise at least four positions that vary across the population, as discussed in detail elsewhere herein.

A "DNA polymerase" is an enzyme capable of extending a primer annealed to a template by adding nucleotides to the 3' end of the primer that are complementary to the template (with the understanding that polymerases generally have an error rate, as known in the art).

"3' to 5' exonuclease activity" refers to an enzymatic activity that removes nucleotides from the 3' end of a nucleic acid.

"5' to 3' exonuclease activity" refers to an enzymatic activity that removes nucleotides from the 5' end of a nucleic acid.

An enzyme or polypeptide "lacks" an enzymatic activity if the activity cannot be detected in a standard assay for such activity. For example, an exonuclease activity can be assayed by providing a suitable nucleic acid substrate in which the 3' or 5' terminal nucleotide, as the case may be, is labeled, and determining whether the enzyme detectably removes the label. The designation "exo-" is used herein as shorthand for a polymerase that lacks exonuclease activity.

A "tag" refers to any sequence added to a nucleic acid molecule, e.g., via incorporation of a 5' element of a primer or via ligation. Tags may have various functions, including serving as binding sites for primers in subsequent reactions or serving as a barcode or index that provides information about the sample or processing of a molecule or identifies the molecule (independently or in combination with the endogenous sequence of the molecule) and replication or amplification products thereof.

"Cell free DNA" ("cfDNA") refers to DNA not contained within a cell at the time of its isolation from a subject.

"Purifying" refers to separating an analyte of interest, such as a repaired DNA molecule, from at least one other component of a composition, e.g., primers, enzyme, salt, nucleotides, and the like. "Purifying" encompasses any procedure in which the separation results in a composition comprising the analyte of interest at a concentration ratio relative to the other component(s) that is higher than in the starting composition.

"Epigenetically modified" DNA comprises one or more modifications of its nucleotides that originated in vivo. 5-methylation and 5-hydroxymethylation of cytosine are examples of epigenetically modified DNA.

DETAILED DESCRIPTION

1. Overview

Samples of nucleic acid often contain partially double-stranded nucleic acid fragments with single-stranded overhangs that require processing in order to prepare them for sequencing, such as high-throughput or next-generation sequencing. While 5' overhangs can be repaired in a simple extension reaction (see FIG. 1), which does not result in loss of sequence information, conventional repair of 3' overhangs has relied upon exonucleolysis, which does eliminate sequence from the fragment.

The invention provides improved methods of repairing 3' overhangs, e.g., that can retain the sequence of all or a substantial part of a 3' overhang. In some embodiments, the methods comprise contacting the partially double-stranded DNA fragment comprising a 3' overhang with one or more primers of a primer population, wherein primer population comprises a random target-hybridizing sequence. One or more members of the primer population can anneal to the partially double-stranded DNA fragment and undergo extension, thereby producing one or more extended primers annealed to the DNA fragment. An extended primer annealed to the DNA fragment together with the 5' end of another extended primer or a strand of the partially double-stranded DNA fragment can form a substrate for ligation. Ligation then provides the repaired DNA fragment. Those skilled in the art will be familiar with appropriate conditions for each of the individual manipulations of such methods, e.g., annealing primers with a random target-hybridizing sequence to a DNA molecule, extending the primers to the 5' end of another segment of DNA, and ligating the extended primers to that 5' end.

In some embodiments, a primer is extended up to the 5' end of a strand of the partially double-stranded DNA fragment and then is ligated to the 5' end of the strand of the partially double-stranded DNA fragment. In some embodiments, a first primer is extended up to the 5' end of a strand of the partially double-stranded DNA fragment; a second primer is extended up to the 5' end of the first primer; and then the first primer is ligated to the 5' end of the strand of the partially double-stranded DNA fragment and the second primer is ligated to the 5' end of the first primer.

In some embodiments, at least steps (a)-(c) of the methods described herein are performed in a single tube.

In some embodiments, the double-stranded DNA fragment is in a composition and for at least steps (a)-(c) no component is removed from the composition.

2. Partially Double-Stranded DNA Fragments

In some embodiments, the partially double-stranded DNA fragment has 3' overhangs at each end. In some embodiments, the partially double-stranded DNA fragment has a 3' overhang and (i) a blunt end or (ii) a 5' overhang. In some embodiments, the 5' overhang is repaired by extending the 3' end along the 5' overhang.

In some embodiments, the partially double-stranded DNA fragment is a cfDNA fragment. In some embodiments, the partially double-stranded DNA fragment is mammalian. In some embodiments, the partially double-stranded DNA fragment is human. In some embodiments, the partially double-stranded DNA fragment is from a bodily fluid sample. In further embodiments, the bodily fluid is whole blood, serum, or plasma.

In some embodiments, the partially double-stranded DNA fragment is part of a population of DNA fragments in a composition. In further embodiments, the population of DNA fragments comprise sheared DNA. In further embodiments, the population of DNA fragments comprise epigenetically modified DNA. In some embodiments, the population of DNA fragments comprises fragments from a plurality of genomic loci, e.g., at least 10, 100, 1000, or 10000 genomic loci. In some embodiments, the population of DNA fragments is non-enriched. A population is non-enriched when it has not been subjected to a procedure that increases the prevalence of some fragments relative to others, such as amplification with sequence-specific primers or target capture with sequence-specific capture probes. In some embodiments, the population of DNA fragments is unamplified, meaning that it has not undergone any amplification procedure. Unamplified DNA can be used to retain epigenetic information such as DNA methylation.

In some embodiments, the partially double-stranded DNA fragment is contained in or obtained from a sample. A sample can be any biological sample isolated from a subject. Samples can include body tissues, such as known or suspected solid tumors, whole blood, platelets, serum, plasma, stool, red blood cells, white blood cells or leucocytes, endothelial cells, tissue biopsies, cerebrospinal fluid synovial fluid, lymphatic fluid, ascites fluid, interstitial or extracellular fluid, the fluid in spaces between cells, including gingival crevicular fluid, bone marrow, pleural effusions, cerebrospinal fluid, saliva, mucous, sputum, semen, sweat, urine. Samples are preferably body fluids, particularly blood and fractions thereof, and urine. A sample can be in the form originally isolated from a subject or can have been subjected to further processing to remove or add components, such as cells, or enrich for one component relative to another. In some embodiments, the partially double-stranded DNA fragment is from a bodily fluid sample. In further embodiments, the bodily fluid is whole blood, serum, or plasma.

In some embodiments, the partially double-stranded DNA fragment is from a plasma sample. The volume of plasma can depend on the desired read depth for sequenced regions. Exemplary volumes are 0.4-40 mL, 5-20 mL, 10-20 mL. For examples, the volume can be 0.5 mL, 1 mL, 5 mL 10 mL, 20 mL, 30 mL, or 40 mL. A volume of sampled plasma may be for example 5 to 20 mL.

A sample can comprise various amount of DNA that contains genome equivalents. For example, a sample of about 30 ng DNA can contain about 10,000 haploid human genome equivalents and, in the case of cell-free DNA (cfDNA), about 200 billion individual nucleic acid molecules. Similarly, a sample of about 100 ng of DNA can contain about 30,000 haploid human genome equivalents and, in the case of cell-free DNA (cfDNA), about 600 billion individual molecules. Some samples contain 1-500, 2-100, 5-150 ng cell-free DNA, e.g., 5-30 ng, or 10-150 ng cell-free DNA.

A sample can comprise DNA from different sources. For example, a sample can comprise germline DNA or somatic DNA. A sample can comprise DNA carrying mutations. For example, a sample can comprise DNA carrying germline mutations and/or somatic mutations. A sample can also comprise DNA carrying cancer-associated mutations (e.g., cancer-associated somatic mutations).

Exemplary amounts of cell-free DNA (cfDNA) in a sample before amplification range from about 1 fg to about 1 ug, e.g., 1 pg to 200 ng, 1 ng to 100 ng, 10 ng to 1000 ng. For example, the amount can be up to about 600 ng, up to about 500 ng, up to about 400 ng, up to about 300 ng, up to about 200 ng, up to about 100 ng, up to about 50 ng, or up to about 20 ng of cell-free nucleic acid molecules. The amount can be at least 1 fg, at least 10 fg, at least 100 fg, at least 1 pg, at least 10 pg, at least 100 pg, at least 1 ng, at least 10 ng, at least 100 ng, at least 150 ng, or at least 200 ng of cell-free nucleic acid molecules. The amount can be up to 1 femtogram (fg), 10 fg, 100 fg, 1 picogram (pg), 10 pg, 100 pg, 1 ng, 10 ng, 100 ng, 150 ng, or 200 ng of cell-free DNA molecules. The method can comprise obtaining 1 femtogram (fg) to 200 ng.

In some embodiments, the body fluid sample is 5-10 ml of whole blood, plasma or serum, which includes about 30 ng of DNA or about 10,000 haploid genome equivalents.

In some embodiments, the partially double-stranded DNA fragment is part of a population of DNA fragments in a composition. In further embodiments, the population of DNA fragments comprise sheared DNA. In some embodiments, the partially double-stranded DNA fragment is a cfDNA fragment.

Cell-free DNA are DNA not contained within or otherwise bound to a cell or in other words nucleic acids remaining in a sample after removing intact cells. Cell-free DNA can be double-stranded, single-stranded, or a hybrid thereof. In some embodiments, the cfDNA fragment comprise double-stranded DNA molecules at least some of which have single-stranded overhangs. A cell-free DNA can be released into bodily fluid through secretion or cell death processes, e.g., cellular necrosis and apoptosis. Some cell-free DNA are released into bodily fluid from cancer cells e.g., circulating tumor DNA (ctDNA). Others are released from healthy cells.

A cell-free DNA can have one or more epigenetic modifications, for example, a cell-free nucleic acid can be acetylated, methylated, ubiquitinylated, phosphorylated, sumoylated, ribosylated, and/or citrullinated. In some embodiments, the partially double-stranded DNA fragment is part of a population of DNA fragments in a composition, where the population of DNA fragments comprise epigenetically modified DNA. Cell-free DNA have a size distribution of about 100-500 nucleotides, particularly 110 to about 230 nucleotides, with a mode of about 168 nucleotides and a second minor peak in a range between 240 to 440 nucleotides.

Cell-free DNA can be isolated from bodily fluids through a partitioning step in which cell-free DNA, as found in solution, are separated from intact cells and other non-soluble components of the bodily fluid. Partitioning may include techniques such as centrifugation or filtration. Alternatively, cells in bodily fluids can be lysed and cell-free and cellular nucleic acids processed together. Generally, after addition of buffers and wash steps, nucleic acids can be precipitated with an alcohol. Further clean up steps may be used such as silica based columns to remove contaminants or salts. Non-specific bulk carrier nucleic acids, for example, may be added throughout the reaction to optimize certain aspects of the procedure such as yield.

After such processing, samples can include various forms of DNA including double-stranded DNA, and single-stranded DNA. Optionally, single stranded DNA can be converted to double stranded forms so they are included in subsequent processing and analysis steps.

3. DNA Polymerases

In some embodiments, the DNA polymerase lacks 3' to 5' exonuclease activity. In some embodiments, the DNA polymerase lacks 5' to 3' exonuclease activity. In some embodiments, the DNA polymerase lacks strand displacement activity. Any DNA polymerase known in the art that is capable of 5'-3' polymerase activity and that lacks 3' to 5' exonuclease activity, 5' to 3' exonuclease activity, and strand displacement activity may be used as the DNA polymerase for step (b) of the methods described herein. In some embodiments, the DNA polymerase is a Klenow fragment. In some embodiments, the DNA polymerase is an exo-Klenow fragment.

4. Primers

In some embodiments, the primers of the primer population are single-stranded.

In some embodiments, the primers of the primer population comprise a hairpin or double-stranded region. In some embodiments, the primers of the primer population are double-stranded with a 3' overhang and the random target-hybridizing sequence is in the 3' overhang. In some embodiments, the primers of the primer population are hairpins with a 3' overhang and the random target-hybridizing sequence is in the 3' overhang.

In some embodiments, the primers of the primer population comprise an adapter. In some embodiments, the hairpin or double-stranded region of the primers comprise an adapter.

In some embodiments, the adapter includes a tag as described herein. In some embodiments, the adapter comprises a tag. In further embodiments, the tag comprises a barcode. In further embodiments, the primer population comprises a plurality of different barcodes.

The same or different adapters can be linked to the respective ends of a repaired DNA fragment. Sometimes the same adapter is linked to the respective ends except that the tag is different. In some embodiments, the adapter is a Y-shaped adapter. In some embodiments, the adapter is a bell-shaped adapter. Adapters used herein are further described below (Section 6).

In some embodiments, the random target-hybridizing sequence has a length of at least 4, 5, 6, 7, 8, 9, or 10 nucleotides. In some embodiments, the random target-hybridizing sequence has a length of at least 4 nucleotides. In some embodiments, the random target-hybridizing sequence has a length of at least 5 nucleotides. In some embodiments, the random target-hybridizing sequence has a length of at least 6 nucleotides. In some embodiments, the random target-hybridizing sequence has a length of at least 7 nucleotides. In some embodiments, the random target-hybridizing sequence has a length of at least 8 nucleotides. In some embodiments, the random target-hybridizing sequence has a length of at least 9 nucleotides. In some embodiments, the random target-hybridizing sequence has a length of at least 10 nucleotides.

In some embodiments, the random target-hybridizing sequence has a length of about 4, 5, 6, 7, 8, 9, 10, 11, or 12 nucleotides. In some embodiments, the random target-hybridizing sequence has a length of about 4 nucleotides. In some embodiments, the random target-hybridizing sequence has a length of about 5 nucleotides. In some embodiments, the random target-hybridizing sequence has a length of about 6 nucleotides. In some embodiments, the random target-hybridizing sequence has a length of about 7 nucleotides. In some embodiments, the random target-hybridizing sequence has a length of about 8 nucleotides. In some embodiments, the random target-hybridizing sequence has a length of about 9 nucleotides. In some embodiments, the random target-hybridizing sequence has a length of about 10 nucleotides. In some embodiments, the random target-hybridizing sequence has a length of about 11 nucleotides. In some embodiments, the random target-hybridizing sequence has a length of about 12 nucleotides.

In any embodiment described herein, the primer population may comprise members wherein each of four different bases (e.g., A, C, T, and G) appear at each position of the random target-hybridizing sequence. Put another way, in different members of the primer population, each of the four bases can appear at each position of the random target-hybridizing sequence. One skilled in the art would recognize that U may be used in place of T, and/or modified bases (e.g., methylated cytosine, pseudouridine, etc.) with the same base pairing preference as an unmodified may be used; as such, T encompasses U and A, C, T, and G each encompass modified forms thereof that retain the same base pairing preference as the unmodified base.

In some embodiments, the partially double-stranded DNA fragment comprises two 3' overhangs which are each repaired as disclosed herein.

In some embodiments, the partially double-stranded DNA fragment comprises a 3' overhang and a 5' overhang. The 5' overhang may be repaired, e.g., by extending the recessed 3' end along the 5' overhang. In some embodiments, this extension is performed by the same polymerase that extends the one or more primers along the 3' overhang.

In some embodiments, the repaired DNA fragment comprises one or two blunt ends. In some embodiments, following the ligation reaction described herein, any remaining overhang is further repaired, e.g., using a suitable exonuclease (e.g., a 3' to 5' exonuclease). This may result in loss of a small amount of sequence but nonetheless retains a substantial amount of sequence that was originally part of a 3' overhang, while still providing a molecule with blunt ends that can be subjected to further manipulation.

In some embodiments, the repaired DNA fragment is subjected to end-tailing, e.g., using a polymerase that performs a non-template directed addition of a nucleotide to the 3' ends of blunt-ended nucleic acids, optionally wherein A is added preferentially to G preferentially to C or T. This polymerase may lack a proof-reading function and/or may be thermostable such as to remain active at the elevated temperature. Taq, Bst large fragment and Tth polymerases are examples of such a polymerase. Although the reaction mixture typically contains equal molar amounts of each of the four standard nucleotide types from the prior step, the four nucleotide types are not added to the 3' ends in equal proportions. Rather A is added most frequently, followed by G followed by C and T.

Where applicable, the blunt-ending and tailing of repaired DNA fragments can be performed in a single-tube. Blunt-ended nucleic acids need not be separated from the enzyme(s) performing the blunt ending before the tailing reaction occurs. Optionally, all enzymes, nucleotides and other reagents are supplied together before the blunt ending reaction occurs. Supplying together means that all are introduced in the sample sufficiently proximate in time such that all are present when the sample incubation occurs for blunt ending to take place. Optionally, nothing is removed from the samples after supplying the enzymes, nucleotides and other reagents at least until both the blunt ending and end tailing incubations have been completed. Often, the end tailing reaction is performed at a higher temperature than the blunt ending reaction. For example, the blunt ending reaction can be performed at ambient temperature in which the 5'-3' polymerase and 3'-5' exonuclease are active and the thermostable polymerase is inactive or minimally active, and the end tailing reaction performed at an elevated temperature, such as over 60° C., when the 5'-3' polymerase and 3'-5' exonuclease are inactive and the thermostable polymerase is active.

In some embodiments, following repair and/or following any further processing steps, the enzyme(s) (e.g., polymerase, ligase, and/or exonuclease) are denatured, e.g., by heat denaturation. For example, denaturation can be effected by raising the temperature to e.g., 75°-80° C.

5. Linking Repaired DNA Fragments to Adapters

In some embodiments, after repair, with or without subsequent purification of the tailed sample molecules, the tailed sample molecules are contacted with adapters. For example, after tailing of the repaired DNA fragments, the tailed sample molecules may be contacted with adapters tailed with complementary T and C nucleotides at one end of the adapters. In another example, repaired DNA fragments with blunt ends may be contacted with adapters having blunt ends.

Adapters can be formed by separate synthesis and annealing of their respective strands. The additional T and C tails, where used, can thus be added as an extra nucleotide in synthesis of one of the strands. Typically adapters tailed with G and A are not included because although these adapters might anneal with sample molecules tailed with C and T respectively, they would also anneal with other adapters. Adapter molecules and sample molecules bearing complementary nucleotides (i.e., T-A and C-G) at their 3' ends anneal and can be ligated to one another. The percentage of C-tailed adapters relative to T-tailed adapters may range from about 5-40% by moles, for example, 10-35%, 15-25%, 20-35%, 25-35% or about 30%. Because the non-template directed addition of a single nucleotide to the 3' ends of sample molecules does not proceed to completion, the sample may also contain some blunt-ended sample molecules without tailing. These molecules can be recovered by also supplying the sample with adapters having one and preferably only one blunt end. Blunt end adapters can be supplied at a molar ratio of 0.2-20%, or 0.5-15% or 1-10% of adapters with T- and C-tailed adapters. Blunt-ended adapters can be provided at the same time, before, or after the T- and C-tailed adapters. Blunt-ended adapters ligated with blunt-ended sample molecules again resulting in sample molecules flanked on both sides by adapters. These molecules lack the A-T or C-G nucleotide pairs between sample and adapters present when tailed sample molecules are ligated to tailed adapters.

The adapters used in these reactions preferably have one and only one end tailed with T or C or one and only one end blunt so that they can ligate with sample molecules in only one orientation. The adapters can be for example Y-shaped adapters in which one end is tailed or blunt and the other end has two single strands. Exemplary Y-shaped adapters have sequences as follows with (6 bases) indicating a tag. The upper oligonucleotide includes a single base T tail.

Universal Adapter:
(SEQ ID NO. 1)
5' AATGATACGGCGACCACCGAGATCTACACTCTTTCCCTACACGACGC
TCTTCCGATCT.

Adapter, Index 1-12:
(SEQ ID NO. 2)
5' GATCGGAAGAGCACACGTCTGAACTCCAGTCAC (6 bases)
ATCTCGTATGCCGTCTTCTGCTTG Another Y-shaped adapter with a C tail has the sequences:

(SEQ ID NO. 3)
5' AATGATACGGCGACCACCGAGATCTACACTCTTTCCCTACACGACGC
TCTTCCGATCC
and Adapter, Index 1-12:
(SEQ ID NO. 2)
5' GATCGGAAGAGCACACGTCTGAACTCCAGTCAC (6 bases)
ATCTCGTATGCCGTCTTCTGCTTG Customized combinations of such oligonucleotide including oligonucleotides with both T and C tails can be synthesized for use in the present methods.

A truncated version of these adapter sequences has been described by Rohland et al., Genome Res. 2012 May; 22(5): 939-946.

Adapters can also be bell-shaped with only one end, which is tailed or blunt. Adapters can include a primer binding site for amplification, a binding site for a sequencing primer, and/or a nucleic acid tag for purposes of identification. The same or different adapters can be used in in a single reaction.

When adapters include an identification tag and nucleic acids in a sample are attached to adapters at each end, the number of potential combinations of identifiers increases exponentially with the number of unique tags supplied (i.e., $n^n$ combinations, where n is the number of unique identification tags). In some methods, the number of combinations of unique tags is sufficient that it is statistically probable that all or substantially all (e.g., at least 90%) of different double-stranded DNA molecules in the sample receive a different combination of tags. In some methods, the number of unique combinations of identifier tags is less than the number of unique double-stranded DNA molecules in the sample (e.g., 5-10,000 different tag combinations).

A kit providing suitable enzymes for performing the above methods is the NEBNext® Ultra™ II DNA Library Prep Kit for Illumina®. The kit provides the following reagents: NEBNext Ultra II End Prep Enzyme Mix, NEBNext Ultra II End Prep Reaction Buffer, NEBNext Ligation Enhancer, NEBNext Ultra II Ligation Master Mix-20, NEBNext® Ultra II Q5® Master Mix.

Attachment of T- and C-tailed adapters as described can result in a population of adapted nucleic acids the population comprising a plurality of nucleic acid molecules each of which comprises a nucleic acid fragment flanked on both sides by an adapter including a bar code with an A/T or G/C base pair between the nucleic acid fragment and adapter. The plurality of nucleic acid molecules can be at least, 10,000, 100,000 or 1,000,000 molecules. Most nucleic acids in the population can be flanked by adapters with different bar codes (e.g., at least 99%). If blunt ended adapters are also included, then the population includes nucleic acid molecules in a nucleic acid fragment is directly joined at either or both ends to an adapter (i.e., no intervening A/T or G/C pair).

6. Amplification

Repaired DNA fragments flanked by adapters can be amplified by PCR or another amplification method, e.g., primed from primers binding to primer binding sites in adapters flanking a nucleic acid to be amplified. Amplification methods can involve cycles of extension, denaturation and annealing resulting from thermocycling or can be isothermal as in transcription mediated amplification. Other amplification methods include the ligase chain reaction, strand displacement amplification, nucleic acid sequence based amplification, and self-sustained sequence based replication.

In some embodiments, the methods described herein further comprises, after step (a)-(c), amplifying the repaired DNA fragments. In further embodiments, the repaired DNA fragment comprises one or more adapters (e.g., two adapters) and amplifying the repaired DNA fragment uses one or more (e.g., two) amplification oligomers that anneal to the one or more adapters.

Where an enrichment step is performed (as discussed elsewhere herein), amplification may precede and/or follow the enrichment step. In some embodiments, the methods comprise amplifying the repaired fragments, performing an enrichment step to provide enriched fragments, and then further amplifying the enriched repaired fragments.

7. Tags

In some embodiments, the nucleic acid molecules (from the sample of polynucleotides) may be tagged with sample indexes and/or molecular barcodes (referred to generally as "tags"). Tags may be incorporated into or otherwise joined to adapters by chemical synthesis, ligation (e.g., blunt-end ligation or sticky-end ligation), or overlap extension polymerase chain reaction (PCR), among other methods. Such adapters may be ultimately joined to the target nucleic acid molecule. In other embodiments, one or more rounds of amplification cycles (e.g., PCR amplification) are generally applied to introduce sample indexes to a nucleic acid molecule using conventional nucleic acid amplification methods. The amplifications may be conducted in one or more reaction mixtures (e.g., a plurality of microwells in an array). Molecular barcodes and/or sample indexes may be introduced simultaneously, or in any sequential order. In some embodiments, molecular barcodes and/or sample indexes are introduced prior to and/or after sequence capturing steps are performed. In some embodiments, only the molecular barcodes are introduced prior to probe capturing and the sample indexes are introduced after sequence capturing steps are performed. In some embodiments, both the molecular barcodes and the sample indexes are introduced prior to performing probe-based capturing steps. In some embodiments, the sample indexes are introduced after sequence capturing steps are performed. In some embodiments, molecular barcodes are incorporated to the nucleic acid molecules (e.g. cfDNA molecules) in a sample through adapters via ligation (e.g., blunt-end ligation or sticky-end ligation). In some embodiments, sample indexes are incorporated to the nucleic acid molecules (e.g. cfDNA molecules) in a sample through overlap extension polymerase chain reaction (PCR). Typically, sequence capturing protocols involve introducing a single-stranded nucleic acid molecule complementary to a targeted nucleic acid sequence, e.g., a coding sequence of a genomic region and mutation of such region is associated with a cancer type.

In some embodiments, the tags may be located at one end or at both ends of the sample nucleic acid molecule. In some embodiments, tags are predetermined or random or semi-random sequence oligonucleotides. In some embodiments, the tags may be less than about 500, 200, 100, 50, 20, 10, 9, 8, 7, 6, 5, 4, 3, 2, or 1 nucleotides in length. The tags may be linked to sample nucleic acids randomly or non-randomly.

In some embodiments, each sample is uniquely tagged with a sample index or a combination of sample indexes. In some embodiments, each nucleic acid molecule of a sample or sub-sample is uniquely tagged with a molecular barcode or a combination of molecular barcodes. In other embodiments, a plurality of molecular barcodes may be used such that molecular barcodes are not necessarily unique to one another in the plurality (e.g., non-unique molecular barcodes). In these embodiments, molecular barcodes are generally attached (e.g., by ligation) to individual molecules such that the combination of the molecular barcode and the sequence it may be attached to creates a unique sequence that may be individually tracked. Detection of non-uniquely tagged molecular barcodes in combination with endogenous sequence information (e.g., the beginning (start) and/or end (stop) positions corresponding to the sequence of the original nucleic acid molecule in the sample, sub-sequences of sequence reads at one or both ends, length of sequence reads, and/or length of the original nucleic acid molecule in the sample) typically allows for the assignment of a unique identity to a particular molecule. The length, or number of base pairs, of an individual sequence read are also optionally used to assign a unique identity to a given molecule. As described herein, fragments from a single strand of nucleic acid having been assigned a unique identity, may thereby permit subsequent identification of fragments from the parent strand, and/or a complementary strand.

In some embodiments, molecular barcodes are introduced at an expected ratio of a set of identifiers (e.g., a combination of unique or non-unique molecular barcodes) to molecules in a sample. One example format uses from about 2 to about 1,000,000 different molecular barcodes, or from about 5 to about 150 different molecular barcodes, or from about 20 to about 50 different molecular barcodes. Alternatively, from about 25 to about 1,000,000 different molecular barcodes may be used. The molecular barcodes can be ligated to both ends of a target molecule. For example, 20-50×20-50 molecular barcodes can be used. In some embodiments, 20-50 different molecular barcodes can be used. In some embodiments, 5-100 different molecular barcodes can be used, In some embodiments, 5-150 molecular barcodes can be used. In some embodiments, 5-200 different molecular barcodes can be used. Such numbers of identifiers are typically sufficient for different molecules having the same start and stop points to have a high probability (e.g., at least 94%, 99.5%, 99.99%, or 99.999%) of receiving different combinations of identifiers. In some embodiments, about 80%, about 90%, about 95%, or about 99% of molecules have the same combinations of molecular barcodes.

In some embodiments, the assignment of unique or non-unique molecular barcodes in reactions is performed using methods and systems described in, for example, U.S. Patent Application Nos. 20010053519, 20030152490, and 20110160078, and U.S. Pat. Nos. 6,582,908, 7,537,898, 9,598,731, and 9,902,992, each of which is hereby incorporated by reference in its entirety. Alternatively, in some embodiments, different nucleic acid molecules of a sample may be identified using only endogenous sequence information (e.g., start and/or stop positions, sub-sequences of one or both ends of a sequence, and/or lengths).

Accordingly, the present disclosure also provides compositions of repaired and tagged DNA fragments produced by a method described herein. The polynucleotides can comprise fragmented DNA, e.g., cfDNA. A set of polynucleotides in the composition that map to a mappable base position in a genome can be non-uniquely tagged, that is, the number of different identifiers can be at least at least 2 and fewer than the number of polynucleotides that map to the mappable base position. A composition of between about 10 ng to about 10 µg (e.g., any of about 10 ng-1 about 10 ng-100 ng, about 100 ng-10 about 100 ng-1 about 1 µg-10 µg) can bear between any of 2, 5, 10, 50 or 100 to any of 100, 1000, 10,000 or 100,000 different identifiers. For example, between 5 and 100 or between 100 and 4000 different identifiers can be used to tag the polynucleotides in such a composition.

Events in which different molecules mapping to the same coordinate (in this case having the same start/stop positions) and bearing the same, rather than different, tags, are referred to as "molecular collisions". In certain instances, the actual number of molecular collisions may be greater than the number of theoretical collisions, calculated, e.g., as above. This may be a function of uneven distribution of molecules across coordinates, differences in efficiency of ligation between barcodes, and other factors. In this case, empirical methods can be used to determine the number of barcodes needed to approach the theoretical collision number. In one embodiment, provided herein is a method of determining a number of barcodes required to diminish barcode collisions for a given haploid genome equivalent based on length distribution of sequenced molecules and sequence uniformity. The method comprising creating a plurality of pools of nucleic acid molecules; tagging each pool with incrementally increasing numbers of barcodes; and determining an optimal number of barcodes that reduces the number of barcode collisions to a theoretical level, e.g., that could be due to differences in affective barcode concentrations due to differences is pooling and ligation efficiency.

In one embodiment, the number of identifiers necessary to substantially uniquely tag polynucleotides mapping to a region can be determined empirically. For example, a selected number of different identifiers can be attached to molecules in a sample, and the number of different identifiers for molecules mapping to the region can be counted. If an insufficient number of identifiers is used, some polynucleotides mapping to the region will bear the same identifier. In that case, the number identifiers counted will be less than the number of original molecules in the sample. The number of different identifiers used can be iteratively increased for a sample type until no additional identifiers, representing new original molecules, are detected. For example, in a first iteration, five different identifiers may be counted, representing at least five different original molecules. In a second iteration, using more barcodes, seven different identifiers are counted, representing at least seven different original molecules. In a third iteration, using more barcodes, 10 different identifiers are counted, representing at least ten different original molecules. In a fourth iteration, using more barcodes, 10 different identifiers, again, are counted. At this point, adding more barcodes is not likely to increase the number of original molecules detected.

8. Enrichment

In some embodiments, a sample comprising DNA fragments is enriched for fragments of interest. For example, enrichment may be performed after ligating extended primers to the 5' end of a strand of the partially double-stranded DNA fragment, or after an amplification step following such ligation and attachment of adapters (either as part of the ligation or in a subsequent step). Enrichment refers to any procedure that increases the relative abundance of fragments of interest versus other fragments, and includes procedures that preferentially retain the fragments of interest in the sample while removing other fragments. The enrichment may be a capture step, e.g., using a set of capture probes that have target-hybridizing sequences specific for the targets of interest. The targets of interest can comprise one or more, or all, of single nucleotide variants, copy number variable regions, fusions, and indels. In some embodiments, one or more, or all, of single nucleotide variants, copy number variable regions, fusions, and indels are associated with a disease or disorder, e.g., a cancer, such as any of the cancers discussed elsewhere herein.

As discussed above, nucleic acids in a sample can be subject to a capture step, in which molecules having target sequences are captured for subsequent analysis. Target capture can involve use of a bait set comprising oligonucleotide baits labeled with a capture moiety, such as biotin or the other examples noted below. The probes can have sequences selected to tile across a panel of regions, such as genes. In some embodiments, a bait set can have higher and lower capture yields for sets of target regions such as those of the sequence-variable target region set and the epigenetic target region set, respectively, as discussed elsewhere herein. Such bait sets are combined with a sample under conditions that allow hybridization of the target molecules with the baits. Then, captured molecules are isolated using the capture moiety. For example, a biotin capture moiety by bead-based streptavidin. Such methods are further described in, for example, U.S. Pat. No. 9,850,523, issuing Dec. 26, 2017, which is incorporated herein by reference.

Capture moieties include, without limitation, biotin, avidin, streptavidin, a nucleic acid comprising a particular nucleotide sequence, a hapten recognized by an antibody, and magnetically attractable particles. The extraction moiety can be a member of a binding pair, such as biotin/streptavidin or hapten/antibody. In some embodiments, a capture moiety that is attached to an analyte is captured by its binding pair which is attached to an isolatable moiety, such as a magnetically attractable particle or a large particle that can be sedimented through centrifugation. The capture moiety can be any type of molecule that allows affinity separation of nucleic acids bearing the capture moiety from nucleic acids lacking the capture moiety. Exemplary capture moieties are biotin which allows affinity separation by binding to streptavidin linked or linkable to a solid phase or an oligonucleotide, which allows affinity separation through binding to a complementary oligonucleotide linked or linkable to a solid phase.

9. Exemplary Workflows to Prepare a Sample for Sequencing

In some embodiments, methods described herein comprise producing repaired DNA fragments according to any of the embodiments described above, wherein adapters are incorporated through the ligation step or a subsequent step. The adapters comprise primer binding sites and optionally barcodes. The repaired DNA fragments comprising adapters are subjected to an amplification reaction. The amplification reaction may be followed by an enrichment step as described herein. The enrichment step may optionally be followed by a further amplification step. In some embodiments, a further tag (e.g., a sample index) is added during the amplification reaction or the further amplification step. These workflows can prepare a sample for sequencing by including one or both of barcodes and a sample index in the repaired fragments, and also enriching the repaired fragments for fragments of interest.

10. Sequencing

In some embodiments, the methods described herein further comprises sequencing the repaired DNA fragment. In further embodiments, the sequencing sequences a nucleotide that formed a 3' overhang in the partially double-stranded DNA fragment.

Repaired DNA fragments flanked by adapters with or without prior amplification can be subject to sequencing. Sequencing methods include, for example, Sanger sequencing, high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing, Single Molecule Sequencing by Synthesis (SMSS) (Helicos), massively-parallel sequencing, Clonal Single Molecule Array (Solexa), shotgun sequencing, Ion Torrent, Oxford Nanopore, Roche Genia, Maxim-Gilbert sequencing, primer walking, sequencing using PacBio, SOLiD, Ion Torrent, or Nanopore platforms. Sequencing reactions can be performed in a variety of sample processing units, which may multiple lanes, multiple channels, multiple wells, or other mean of processing multiple sample sets substantially simultaneously. Sample processing unit can also include multiple sample chambers to enable processing of multiple runs simultaneously. In some embodiments, a plurality of repaired DNA fragments are generated and at least a portion of the repaired DNA fragments comprise tags, and the sequencing generates a plurality of sequence reads from a plurality of repaired DNA fragments. In some embodiments, the sequence reads comprise sequence of nucleotides that formed a 3' overhang in the partially double-stranded DNA fragment and sequence of a tag.

The sequencing reactions can be performed on one more fragments types known to contain markers of cancer or other disease. The sequencing reactions can also be performed on any nucleic acid fragments present in the sample. The sequence reactions may provide for sequence coverage of the genome of at least 5%, 10%, 15%, 20%, 25%, 30%, 40%, 50%, 60%, 70%, 80%, 90%, 95%, 99%, 99.9% or 100%. In other cases, sequence coverage of the genome may be less than 5%, 10%, 15%, 20%, 25%, 30%, 40%, 50%, 60%, 70%, 80%, 90%, 95%, 99%, 99.9% or 100%.

Simultaneous sequencing reactions may be performed using multiplex sequencing. In some cases, cell-free nucleic acids may be sequenced with at least 1000, 2000, 3000, 4000, 5000, 6000, 7000, 8000, 9000, 10000, 50000, 100,000 sequencing reactions. In other cases, cell-free polynucleotides may be sequenced with less than 1000, 2000, 3000, 4000, 5000, 6000, 7000, 8000, 9000, 10000, 50000, 100,000 sequencing reactions. Sequencing reactions may be performed sequentially or simultaneously. Subsequent data analysis may be performed on all or part of the sequencing reactions. In some cases, data analysis may be performed on at least 1000, 2000, 3000, 4000, 5000, 6000, 7000, 8000, 9000, 10000, 50000, 100,000 sequencing reactions. In other cases, data analysis may be performed on less than 1000, 2000, 3000, 4000, 5000, 6000, 7000, 8000, 9000, 10000, 50000, 100,000 sequencing reactions.

The sequencing method can be massively parallel sequencing, that is, simultaneously (or in rapid succession) sequencing any of at least 100, 1000, 10,000, 100,000, 1 million, 10 million, 100 million, or 1 billion nucleic acid molecules.

11. Analysis

The present methods can be used to diagnose presence or absence of conditions, particularly cancer, in a subject, to characterize conditions (e.g., staging cancer or determining heterogeneity of a cancer), monitor response to treatment of a condition, or determine the risk of recurrence for a condition in a subject.

Various cancers may be detected using the present methods. Cancer cells, as most cells, can be characterized by a rate of turnover, in which old cells die and replaced by newer cells. Generally dead cells, in contact with vasculature in a given subject, may release DNA or fragments of DNA into the blood stream. This is also true of cancer cells during various stages of the disease. Cancer cells may also be characterized, dependent on the stage of the disease, by various genetic aberrations such as copy number variation as well as rare mutations. This phenomenon may be used to detect the presence or absence of cancers in individuals using the methods and systems described herein.

The types and number of cancers that may be detected may include blood cancers, brain cancers, lung cancers, skin cancers, nose cancers, throat cancers, liver cancers, bone cancers, lymphomas, pancreatic cancers, skin cancers, bowel cancers, rectal cancers, thyroid cancers, bladder cancers, kidney cancers, mouth cancers, stomach cancers, solid state tumors, heterogeneous tumors, homogenous tumors and the like.

Cancers can be detected from genetic variations including mutations, rare mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, abnormal changes in nucleic acid methylation infection and cancer.

Genetic data can also be used for characterizing a specific form of cancer. Cancers are often heterogeneous in both composition and staging. Genetic profile data may allow characterization of specific sub-types of cancer that may be important in the diagnosis or treatment of that specific sub-type. This information may also provide a subject or practitioner clues regarding the prognosis of a specific type of cancer and allow either a subject or practitioner to adapt treatment options in accord with the progress of the disease. Some cancers progress, becoming more aggressive and genetically unstable. Other cancers may remain benign, inactive or dormant. The system and methods of this disclosure may be useful in determining disease progression.

The present analysis is also useful in determining the efficacy of a particular treatment option. Successful treatment options may increase the amount of copy number variation or rare mutations detected in subject's blood if the treatment is successful as more cancers may die and shed DNA. In other examples, this may not occur. In another example, perhaps certain treatment options may be correlated with genetic profiles of cancers over time. This correlation may be useful in selecting a therapy. Additionally, if a cancer is observed to be in remission after treatment, the present methods can be used to monitor residual disease or recurrence of disease.

The present methods can also be used for detecting genetic variations in conditions other than cancer. Immune cells, such as B cells, may undergo rapid clonal expansion upon the presence certain diseases. Clonal expansions may be monitored using copy number variation detection and certain immune states may be monitored. In this example, copy number variation analysis may be performed over time to produce a profile of how a particular disease may be progressing. Copy number variation or even rare mutation detection may be used to determine how a population of pathogens are changing during the course of infection. This may be particularly important during chronic infections, such as HIV/AIDS or Hepatitis infections, whereby viruses may change life cycle state and/or mutate into more virulent forms during the course of infection. The present methods may be used to determine or profile rejection activities of the host body, as immune cells attempt to destroy transplanted tissue to monitor the status of transplanted tissue as well as altering the course of treatment or prevention of rejection.

Further, the methods of the disclosure may be used to characterize the heterogeneity of an abnormal condition in a subject, the method comprising generating a genetic profile of extracellular polynucleotides in the subject, wherein the genetic profile comprises a plurality of data resulting from copy number variation and rare mutation analyses. In some cases, including but not limited to cancer, a disease may be heterogeneous. Disease cells may not be identical. In the example of cancer, some tumors are known to comprise different types of tumor cells, some cells in different stages of the cancer. In other examples, heterogeneity may comprise multiple foci of disease. Again, in the example of cancer, there may be multiple tumor foci, perhaps where one or more foci are the result of metastases that have spread from a primary site.

The present methods can be used to generate or profile, fingerprint or set of data that is a summation of genetic information derived from different cells in a heterogeneous disease. This set of data may comprise copy number variation and rare mutation analyses alone or in combination.

The present methods can be used to diagnose, prognose, monitor or observe cancers or other diseases of fetal origin. That is, these methodologies may be employed in a pregnant subject to diagnose, prognose, monitor or observe cancers or other diseases in a unborn subject whose DNA and other nucleic acids may co-circulate with maternal molecules.

Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

What is claimed is:

1. A method of repairing a partially double-stranded DNA fragment, the method comprising:

(a) contacting the partially double-stranded DNA fragment with one or more primers of a primer population, wherein the partially double-stranded DNA fragment comprises a 3' overhang and the primer population comprises a random target-hybridizing sequence;

(b) extending one or more primers of the primer population along the DNA fragment using a DNA polymerase, thereby producing one or more extended primers annealed to the DNA fragment; and (c) ligating the 3' end of one or more extended primers to the 5' end of an extended primer or a strand of the partially double-stranded DNA fragment, thereby providing a repaired DNA fragment.

2. The method of claim 1, wherein the DNA polymerase lacks 3' to 5' exonuclease activity.

3. The method of claim 1, wherein the DNA polymerase lacks 5' to 3' exonuclease activity.

4. The method of claim 1, wherein the DNA polymerase lacks strand displacement activity.

5. The method of claim 1, wherein the DNA polymerase is a Klenow fragment.

6. The method of claim 5, wherein the DNA polymerase is an exo-Klenow fragment.

7. The method of claim 1, wherein the partially double-stranded DNA fragment has 3' overhangs at each end.

8. The method of claim 1, wherein the partially double-stranded DNA fragment has a 3' overhang and (i) a blunt end or (ii) a 5' overhang.

9. The method of claim 8, wherein the 5' overhang is repaired by extending the 3' end along the 5' overhang.

10. The method of claim 1, wherein the partially double-stranded DNA fragment is a cfDNA fragment.

11. The method of claim 1, wherein the partially double-stranded DNA fragment is part of a population of DNA fragments in a composition.

12. The method of claim 11, wherein the population of DNA fragments comprise sheared DNA.

13. The method of claim 11, wherein the population of DNA fragments comprise epigenetically modified DNA.

14. The method of claim 11, wherein the population of DNA fragments comprises fragments from a plurality of genomic loci.

15. The method of claim 11, wherein the population of DNA fragments is non-enriched.

16. The method of claim 11, wherein the population of DNA fragments is unamplified.

17. The method of claim 1, wherein the primers of the primer population are single-stranded.

18. The method of claim 1, wherein the primers of the primer population are double-stranded with a 3' overhang and the random target-hybridizing sequence is in the 3' overhang.

19. The method of claim 1, wherein the primers of the primer population are hairpins with a 3' overhang and the random target-hybridizing sequence is in the 3' overhang.

20. The method of claim 17, wherein the hairpin or double-stranded region of the primers comprises a barcode.

\* \* \* \* \*